US012577521B2

(12) United States Patent
Hermsmeier et al.

(10) Patent No.: US 12,577,521 B2
(45) Date of Patent: Mar. 17, 2026

(54) METHOD AND DEVICE FOR CONTROLLING THE FILLING LEVEL IN A CHAMBER

(71) Applicant: Lonza Cologne GmbH, Cologne (DE)

(72) Inventors: Sven Hermsmeier, Bonn (DE); Timo Gleissner, Euskirchen (DE)

(73) Assignee: Lonza Cologne GmbH (DE)

( * ) Notice: Subject to any disclaimer, the term of this patent is extended or adjusted under 35 U.S.C. 154(b) by 1111 days.

(21) Appl. No.: 17/596,089

(22) PCT Filed: May 28, 2020

(86) PCT No.: PCT/EP2020/064799
§ 371 (c)(1),
(2) Date: Dec. 2, 2021

(87) PCT Pub. No.: WO2020/249401
PCT Pub. Date: Dec. 17, 2020

(65) Prior Publication Data
US 2022/0298466 A1      Sep. 22, 2022

(30) Foreign Application Priority Data

Jun. 13, 2019     (EP) ..................................... 19179949

(51) Int. Cl.
*C12M 1/34*          (2006.01)
*C12M 1/00*          (2006.01)
           (Continued)
(52) U.S. Cl.
CPC ............ *C12M 41/44* (2013.01); *C12M 23/34* (2013.01); *C12M 29/26* (2013.01); *C12M 35/02* (2013.01); *G01F 23/24* (2013.01); *G01F 23/804* (2022.01)

(58) Field of Classification Search
CPC ...... C12M 41/44; C12M 23/34; C12M 29/26; C12M 35/02; C12M 45/07; C12M 23/00;
           (Continued)

(56) References Cited

U.S. PATENT DOCUMENTS 6,258,592 B1     7/2001  Ragsdale et al.
6,969,604 B1*  11/2005  Yakovenko ............ C12M 35/02
                                                         435/288.1
           (Continued)

FOREIGN PATENT DOCUMENTS

EP            3138920 A1     3/2017

*Primary Examiner* — John McGuirk
(74) *Attorney, Agent, or Firm* — Agris & von Natzmer LLP; Joyce v. Natzmer

(57) ABSTRACT

The invention relates to a method and device for controlling a filling level of a suspension of cells, cell derivatives, organelles, sub-cellular particles and/or vesicles within at least one chamber of a device for applying an electric field to the suspension. In order to avoid overfilling of the chamber if multiple electroporation cycles are performed and to achieve exact filling in an environment of unpredictable chamber volume, the amount of suspension filled into the chamber is dynamically limited in the course of several electroporation cycles by determining at least one change of the electrical resistance at the outlet port. The resistance between at least one electrode and a grounding electrode is measured during the filling procedure of each cycle at several points in time. Once a change of resistance is detected, the termination routine is initiated and the filling procedure is finally terminated. Exact filling of the chamber is thus ensured during each electroporation cycle so that enhanced reproductive electroporation performance can be guaranteed.

16 Claims, 7 Drawing Sheets

(51) Int. Cl.
  C12M 1/42 (2006.01)
  G01F 23/24 (2006.01)
  G01F 23/80 (2022.01)

(58) Field of Classification Search
  CPC ....... C12M 33/04; C12M 41/00; G01F 23/24;
          G01F 23/804; G01F 23/263; G01F
          23/2921; C12N 13/00
  See application file for complete search history.

(56) References Cited

U.S. PATENT DOCUMENTS

| | | |
|---|---|---|
| 2014/0220665 A1 | 8/2014 | King et al. |
| 2017/0067007 A1* | 3/2017 | Miltenyi ................ A61N 1/327 |
| 2017/0233716 A1* | 8/2017 | Altrogge ................ C12M 35/02 |
| | | 435/173.6 |

* cited by examiner

Liquid handling

METHOD AND DEVICE FOR CONTROLLING THE FILLING LEVEL IN A CHAMBER

PRIORITY

This application is a national phase filing under section 371 of International Application No. PCT/EP2020/064799, filed on May 28, 2020, which claims the benefit of and priority to European Patent Application No. 19179949.3 filed on Jun. 13, 2019, both of which applications are incorporated herein by reference.

BACKGROUND

The invention relates to a method for controlling a filling level of a suspension of cells, cell derivatives, organelles, sub-cellular particles and/or vesicles within at least one chamber of a device for applying an electric field to the suspension. The invention further relates to a device for applying an electric field to a suspension of cells, cell derivatives, organelles, sub-cellular particles and/or vesicles within at least one chamber, comprising at least a first and a second electrode, at least one inlet port disposed at one end of the chamber, and at least one outlet port disposed at the opposite end of the chamber, wherein the first electrode is disposed within the chamber at the inlet port and the second electrode is disposed within the chamber at the outlet port, and wherein the chamber further comprises at least one grounding electrode.

The introduction of biologically active molecules, for example DNA, RNA or proteins, into living cells, cell derivatives, organelles, sub-cellular particles and/or vesicles may, e.g., serve to examine the biological functions of these molecules and is, moreover, an essential precondition for the success of the therapeutic use of these molecules, e.g., in gene therapy. A preferred method for introducing external molecules into the cells is the so-called electroporation, which unlike chemical methods limits undesirable changes in the structure and function of the target cell. In electroporation the external molecules are introduced into the cells from an aqueous solution, preferably a buffer solution specifically adapted to the cells, or a cell culture medium, via a short current flow, i.e., the pulse of a discharging capacitor which renders the cell membrane transiently permeable to the external molecules. The temporary "pores" that are formed in the cell membrane allow the biologically active molecules to first reach the cytoplasm in which they may already perform their function or exert any therapeutic action to be examined, and then, under certain conditions, to also reach the cell nucleus as it is required, e.g., in gene therapy applications. Due to a short application of a strong electrical field, i.e. a short pulse with a high current density, cells, cell derivatives, organelles, sub-cellular particles and/ or vesicles may also be fused. In this so-called electrofusion the cells are, e.g., initially brought into close membrane contact by an inhomogeneous electrical alternating field. The subsequent application of an electrical field pulse leads to interaction between membrane parts, which ultimately results in fusion. Devices comparable to those used for electroporation may be used for electrofusion as well.

During electroporation of cells a certain amount of debris and foam is generated inside the reaction chamber. When the processed cell suspension is being removed from the reaction chamber, e.g., by pushing in air or letting gravity drain the chamber, this debris and foam remains inside the chamber and reduces the filling volume for a new cell suspension that is to be filled into this chamber for another electroporation cycle. That is, the chamber volume can vary and thus render the volume needed for the next filling almost unpredictable. To avoid overfilling of the chamber with precious material that would not be processed this way, it is therefore important to dynamically limit the amount filled into the chamber accordingly. However, filling in less volume preventively to avoid overfilling is causing an insufficient filling that favors the generation of arc discharges at the air-liquid interface. Arc discharges generate heat and high currents that can damage electrical interfaces and components but also harm the biological material inside the reaction chamber. In addition, the end-user of the system is inserting the tubing with an undefined tension to the tubing which results in an unknown inner diameter. If peristaltic pumps are being used, this is again causing an uncertainty in the processed volume per pump rotation. Therefore, an exact filling is to be achieved for a good reproductive electroporation performance.

EP 3 138 920 B1 discloses a method for electroporation of cells and a disposable device for electroporation. The device includes a fluid department for receiving a cell suspension and a fluid comprising a compound to be transferred into the cells. The device further includes a first and a second electrode as well as corresponding grounding electrodes. The fluids are introduced into the fluid compartment to a predefined filling level, wherein the filling level is determined by measuring the capacitance between the first and the second electrode or the electrical resistance between the grounding electrodes. Filling is continued, for example, until the maximum capacity between the electrodes is reached. After electroporation, the processed cell suspension is cleared from the fluid department. By controlling the filling level of the fluid compartment, the device can be operated in a semi-continuous mode. Moreover, in order to treat higher volumes of the cell suspension, the process of filling, electroporation and clearing can be repeated.

However, if multiple electroporation cycles have to be performed, it is still a drawback of the prior art devices and methods that exact filling of the electroporation chamber cannot be guaranteed for all cycles.

SUMMARY

It is an object of the invention to provide a method and device for controlling a filling level of a suspension of cells, cell derivatives, organelles, sub-cellular particles and/or vesicles within at least one chamber of a device for applying an electric field to the suspension, with which overfilling of the chamber can be avoided, even if multiple electroporation cycles are performed, and exact filling can be achieved, even in an environment of unpredictable chamber volume, in order to ensure a good reproductive electroporation performance for all cycles.

The object is met by a method for controlling a filling level of a suspension of cells, cell derivatives, organelles, sub-cellular particles and/or vesicles within at least one chamber of a device for applying an electric field to the suspension, wherein the device comprises at least a first and a second electrode, at least one inlet port disposed at one end of the chamber, and at least one outlet port disposed at the opposite end of the chamber, wherein the first electrode is disposed within the chamber at the inlet port and the second electrode is disposed within the chamber at the outlet port, and wherein the chamber further comprises at least one grounding (counter) electrode, this method comprising:

a) Starting a filling procedure wherein the suspension is charged into the chamber through the inlet port;

b) Measuring the electrical resistance within the chamber between the second electrode and the grounding electrode during the filling procedure at several points in time; and c) Initiating a termination routine comprising terminating the filling procedure, wherein the termination routine is initiated depending on at least one change of the electrical resistance between the second electrode and the grounding electrode.

That is, according to the invention the amount of suspension filled into the chamber is dynamically limited in the course of several electroporation cycles by determining at least one change of the electrical resistance at the outlet port. To this end, the resistance between the second electrode and the grounding electrode, for example, between the electrode disposed next to the outlet port and its counter electrode, is measured during the filling procedure of each cycle at several points in time. Once a change of resistance is detected, the termination routine is initiated and, optionally after a deferred termination routine, the filling procedure is finally terminated. As a result, overfilling of the chamber can be avoided, even if the filling volume of the chamber is continuously reduced in the course of multiple electroporation cycles. Exact filling of the chamber is thus ensured during each electroporation cycle so that enhanced reproductive electroporation performance can be guaranteed. It is another advantage of the method according to the invention that a waste of precious and expensive biological material can be effectively avoided.

In an advantageous embodiment of the invention the termination routine is initiated when the electrical resistance has reached a predetermined value. In cases where debris, residue and bubbles may cause triggering of the termination routine algorithm too early, an empirically determined threshold can be introduced in order to differentiate between residue and real sample effects. In this embodiment the termination routine is only initiated after a predetermined resistance value is reached and/or the resistance has fallen below this value. For example, once the resistance falls below a certain limit (predetermined value), the control system of the device triggers the start of the termination routine.

In a further advantageous embodiment of the invention the filling procedure is terminated if termination conditions are met, said termination conditions comprising:

a first slope of a change of the resistance exceeds a first predetermined threshold, and a second slope of a change of the resistance reaches a second predetermined threshold, wherein the second threshold represents a slope that is lower than the slope represented by the first threshold.

According to this embodiment the amount of suspension filled into the chamber is dynamically limited by determining scopes of changes of the electrical resistance. That is, if the slope of the change of resistance decreases, the termination routine is initiated and, optionally after a deferred termination routine, the filling procedure is finally terminated. For example, once it is determined that the slope of the change in resistance exceeds a specific preset threshold (first threshold), the control system of the device waits for the slope to decrease again until reaching another specific preset threshold (second threshold).

In another advantageous embodiment of the invention the termination conditions further comprise that a third slope of a change of the resistance, which is determined after the second slope, is equal to or lies below the second threshold. Accordingly, the filling procedure is only terminated if the second threshold is reached or underrun for at least two consecutive measurements so as to reduce inaccuracies caused by measurement variations.

In a further advantageous embodiment of the invention the termination routine comprises a deferred termination after it has been determined that the termination conditions are met, wherein the filling procedure is continued before final termination based on at least one preset parameter. By this measure, empirically determined variations in the correlation of resistance and filling level can be effectively compensated. That is, the filling procedure is continued until deviations from the perfect filling amount, which constantly increase from filling to filling, are compensated.

For example, the preset parameter may comprise a number of steps performed by a peristaltic pump. However, any pump (such as syringe or infusion pumps) that is able to precisely control the amount of liquid processed can be used in the method according to the invention. The number of steps of a peristaltic (stepper motor) pump can be calculated, e.g., by the equation $N\_target=(N\_p+N\_sts)/2+P$, wherein $N\_target$ is the calculated number of steps necessary to complete the filling procedure, $N\_p$ is the number of steps performed during the previous filling procedure, $N\_sts$ is the number of the current standard detection target steps, and $P$ is an empirically determined number of steps. The wording "current standard detection target steps" as used herein refers to the targeted number of steps (correlating to pump rotations and thus volume) calculated independently just from the current filling cycle information. This number of steps and the number of steps from the previous cycle are then averaged/smoothed because of natural variations caused by the sample.

If it is established that there is still a deviation from the perfect filling amount, this issue can be addressed by adding further steps (N) of the peristaltic pump to the filling. Accordingly, the number of steps of a peristaltic pump can be calculated, e.g., by the equation $N\_target=((N\_now+S-R)+N\_p)/2+P-N$, wherein $N\_target$ is the calculated number of steps necessary to complete the filling procedure, $N\_now$ is the current number of steps, $S$ is a preset (empirically determined) number of steps, $R$ is a preset number of steps correlating with the energy of an electrical voltage pulse, $N\_p$ is the number of steps performed during the previous filling procedure, $P$ is an empirically determined number of steps, and $N$ is the number of (all previous) filling procedures (cycles) multiplied by 20. The term "current" as used herein refers to the actual number of pump steps performed so far during an ongoing filling when all filling criteria for this filling are met and the control system of the device only has to calculate/predict the remaining steps required for a proper filling.

In a further advantageous embodiment of the invention an initial delivering procedure is started before the filling procedure is started, said delivering procedure comprising mixing the suspension of cells, cell derivatives, organelles, sub-cellular particles and/or vesicles with a substrate or probe at a mixing point upstream of the inlet port, and charging the mixture or the suspension through the inlet port into the chamber until a resistance drop is detected at the first electrode, wherein the electrical resistance is measured within the chamber between the first electrode and a grounding electrode during the initial delivering procedure at several points in time. That is, in this "priming" process the resistance between the first electrode and the grounding electrode, for example, between the electrode disposed next to the inlet port and its counter electrode, is measured. If the infinite electrical resistance of an empty electroporation chamber drops down to a lower value, it is reliably indicated that the liquid (suspension/mixture) has reached the electrode closest to the inlet port. Mixing the suspension with the probe upstream of the inlet port and measuring the resistance at the inlet port ensures that the suspension is perfectly prepared for electroporation before it is introduced into the chamber so as to be independent of the tubing length, the optical properties of the cell suspension and to avoid more complex measurements, such as capacitive methods, during the priming process. In particular, the electrode(s) at the inlet port of the reaction chamber are used to detect liquid-based electrical changes inside the chamber in order to determine when a first portion of the liquid has reached the reaction chamber.

In this embodiment the resistance drop detected at the first electrode may comprise a decrease of the electrical resistance in the range from 5 to 15 Ohms, preferably about 10 Ohms. Accordingly, the resistance threshold for the resistance-based liquid detection of the cell suspension at the inlet port should be, for example, about 10 Ohms below the initial resistance measurement value upon start of priming. As soon as the measured resistance at the first electrode drops by these 10 Ohms, the suspension shall be considered as detected.

In order to ensure complete mixing of the suspension with the substrate or probe the initial delivering procedure further comprises stopping the charging of the suspension into the chamber when the resistance drop is detected and then retracting the suspension back to the mixing point where the suspension is mixed with the substrate or probe before the filling procedure is started. By this measure it is ensured that the suspension is perfectly mixed with the substrate or probe before it enters the chamber for electroporation.

The initial delivering procedure, if any, is only performed once before the first filling procedure is started.

In order to perform electroporation, the electric field is applied to the suspension within the chamber by supplying at least one voltage pulse through at least one electrode after the filling procedure is terminated. Filling the chamber with the suspension and subsequently supplying at least one voltage pulse may be repeated for a predefined number of cycles. Accordingly, in contrast to a batch process, large volumes of the suspension can be treated by continuously repeating electroporation of aliquots of the suspension in a kind of semi-continuous process.

The object is further met by a device for applying an electric field to a suspension of cells, cell derivatives, organelles, sub-cellular particles and/or vesicles within at least one chamber, comprising at least a first and a second electrode, at least one inlet port disposed at one end of the chamber, and at least one outlet port disposed at the opposite end of the chamber, wherein the first electrode is disposed within the chamber at the inlet port and the second electrode is disposed within the chamber at the outlet port, and wherein the chamber further comprises at least one grounding (counter) electrode. According to the invention at least the second electrode is a first sensor electrode for measuring the electrical resistance within the chamber between the second electrode and the grounding electrode. By controlling the electrical resistance at the outlet port, overfilling of the chamber can be avoided, even if the filling volume of the chamber is continuously reduced in the course of multiple electroporation cycles. Exact filling of the chamber is thus ensured during each electroporation cycle so that enhanced reproductive electroporation performance can be guaranteed. It is another advantage of the device according to the invention that a waste of precious and expensive biological material can be effectively avoided.

In an advantageous embodiment of the device according to the invention the first electrode is a second sensor electrode for measuring the electrical resistance within the chamber between the first electrode and the grounding (counter) electrode. By controlling the electrical resistance at the first electrode, it can reliably indicated that the liquid (suspension) has reached the electrode closest to the inlet port. In particular, the electrode(s) at the inlet port of the reaction chamber are used to detect liquid-based electrical changes inside the chamber in order to determine when a first portion of the liquid has reached the reaction chamber.

The invention is further exemplarily described in detail with reference to the figures.

X axis shows the number of measurements taken (interval: about 33 steps of a stepper motor pump);

Y axis shows the electrical resistance measured [Ohm].

Figure 5:
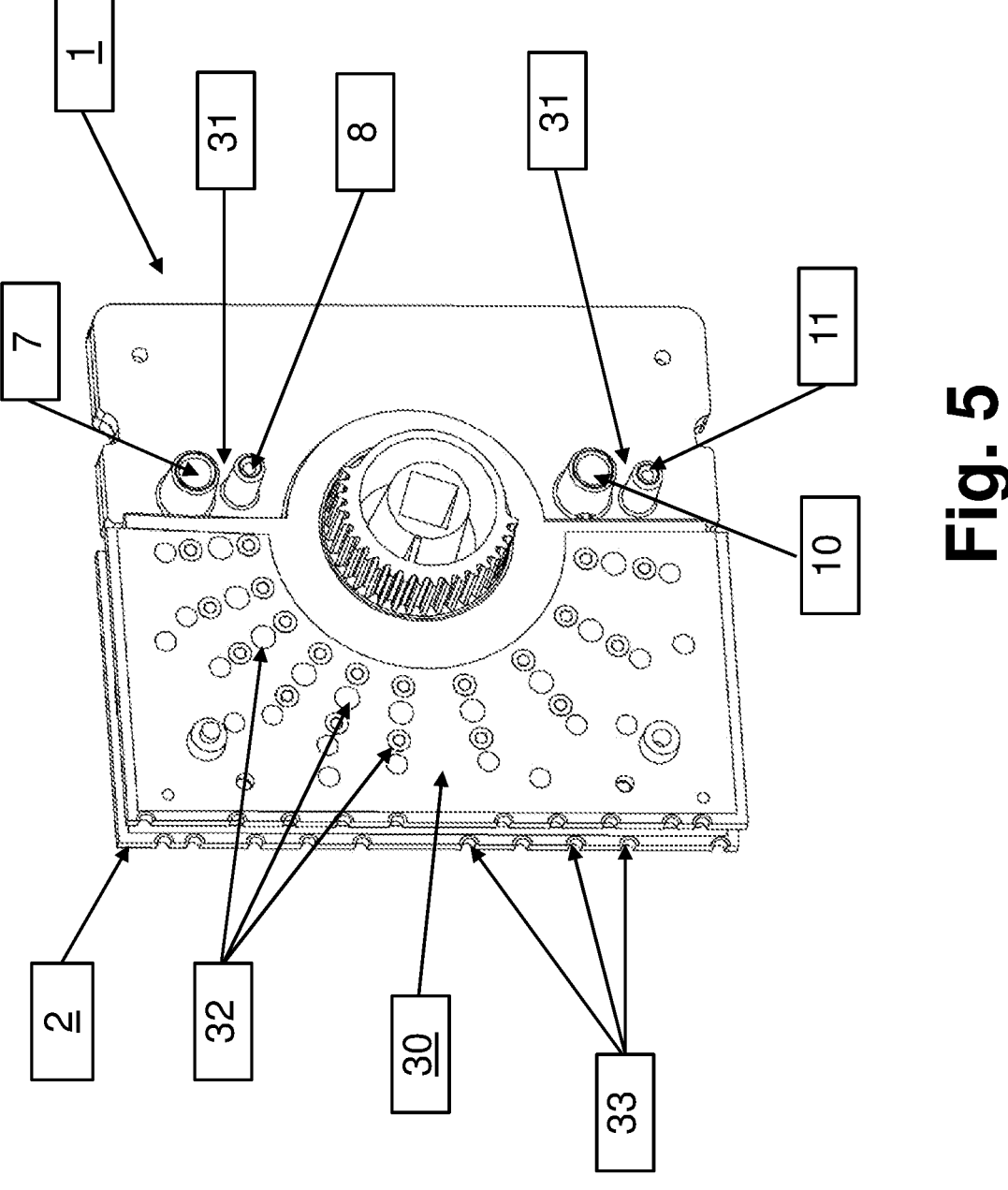

FIG. 5 shows a perspective view of the outer side of an exemplary embodiment of a device according to the invention.

Figure 6:
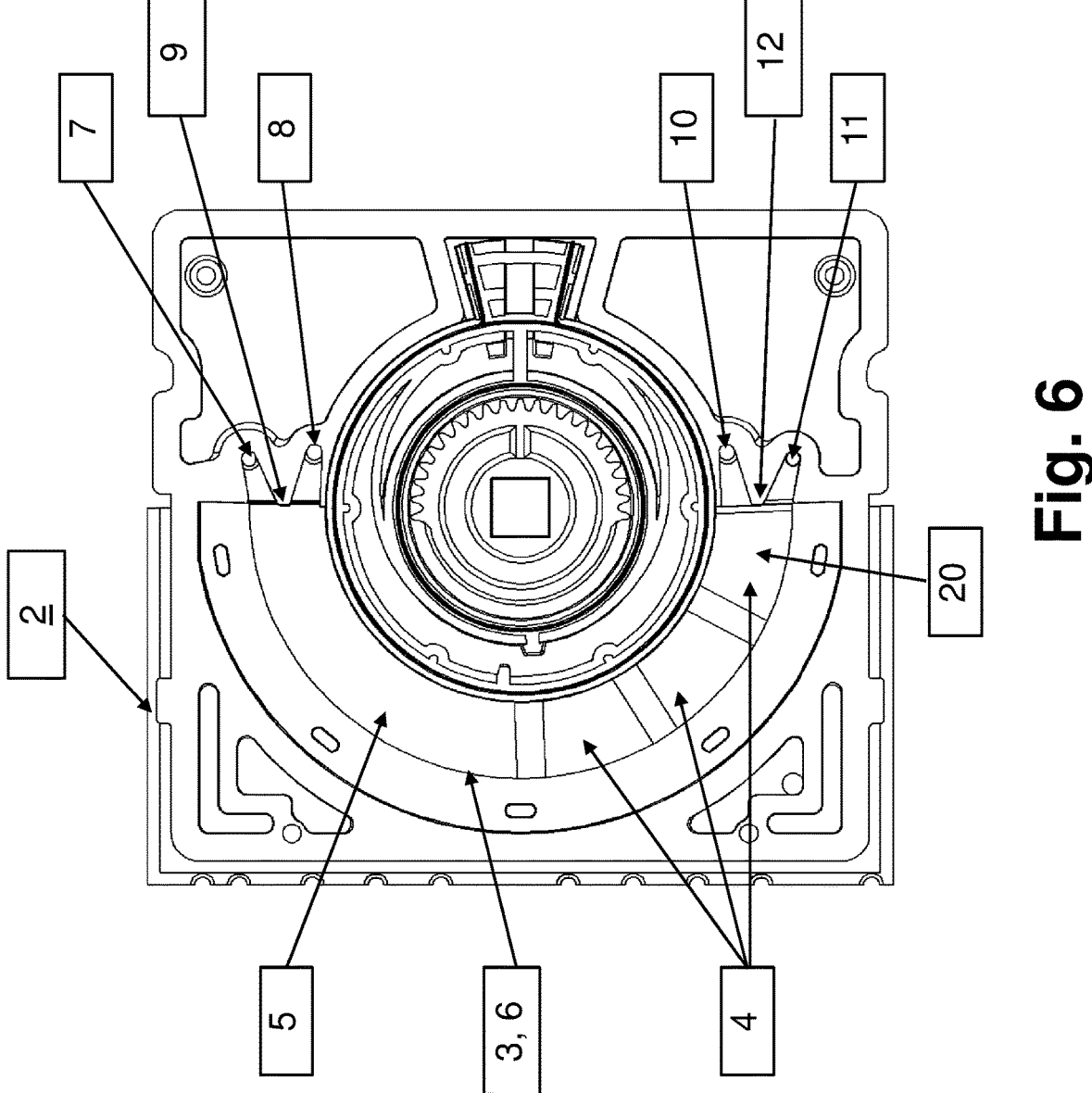

FIG. 6 shows a plan view of the inner side of one component of the device according to FIG. 5.

Figure 7:
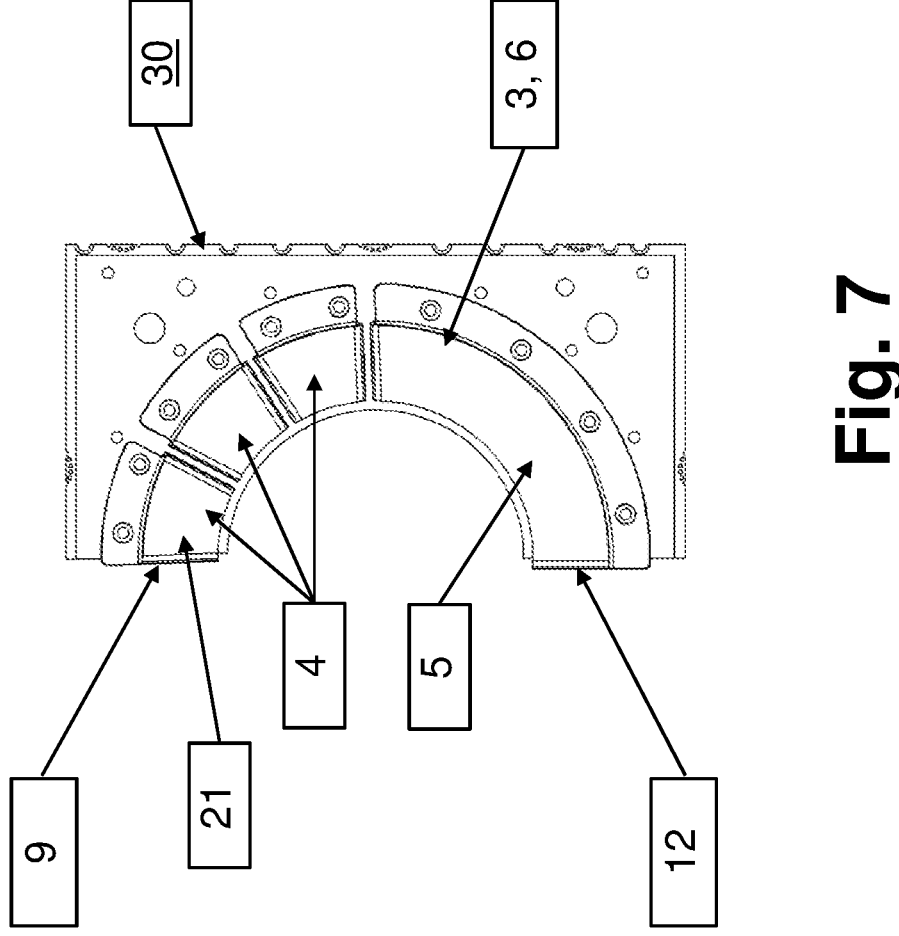

FIG. 7 shows a plan view of the inner side of another component of the device according to FIG. 5.

DETAILED DESCRIPTION OF ILLUSTRATIVE EMBODIMENTS

Figure 1:
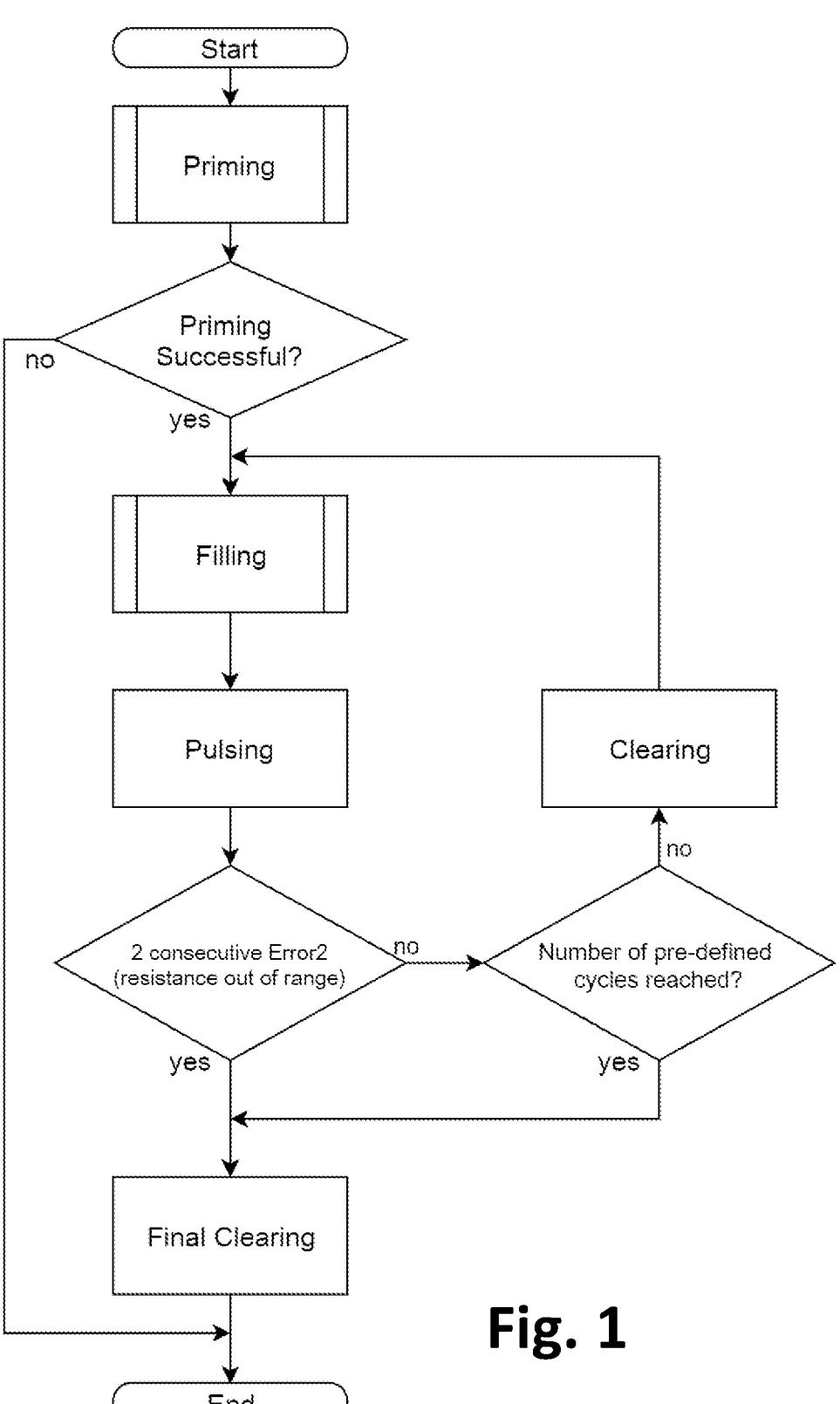
FIG. 1 shows a flow chart representing an exemplary suspension handling procedure of the method according to the invention.

FIG. 1 shows an overview of an embodiment of the entire suspension handling process according to the invention. First, an initial delivering procedure ("priming") is started before the chamber is filled with the suspension. The initial delivering procedure comprises mixing of the suspension with a substrate/probe at a mixing point upstream of the inlet port and charging the mixture through the inlet port into the chamber. This delivering procedure is only performed once before the first filling procedure is started. The initial delivering procedure is further described in detail with reference to FIG. 2. If priming has not been successful, the suspension handling process is terminated. If priming has been successful, the filling procedure is started. The filling procedure comprises charging the suspension/probe mixture into the chamber and controlling the filling level until the optimal filling level is reached. The filling procedure is further described in detail with reference to FIG. 3. Thereafter, electroporation is performed by applying one or more voltage pulse(s) to the mixture ("pulsing"). After pulsing, and if the preset number of cycles has not yet been reached, the chamber is cleared and the second (next) aliquot of the mixture is filled into the chamber for electroporation. The filling and pulsing process can be repeated several times, that is, for a preset number of cycles. If the preset number of cycles is reached, or the electrical resistance measured between two electrodes within the chamber is out of range for two consecutive measurements ("Error2"), the chamber is cleared and the suspension handling process is finally terminated.

Figure 2:
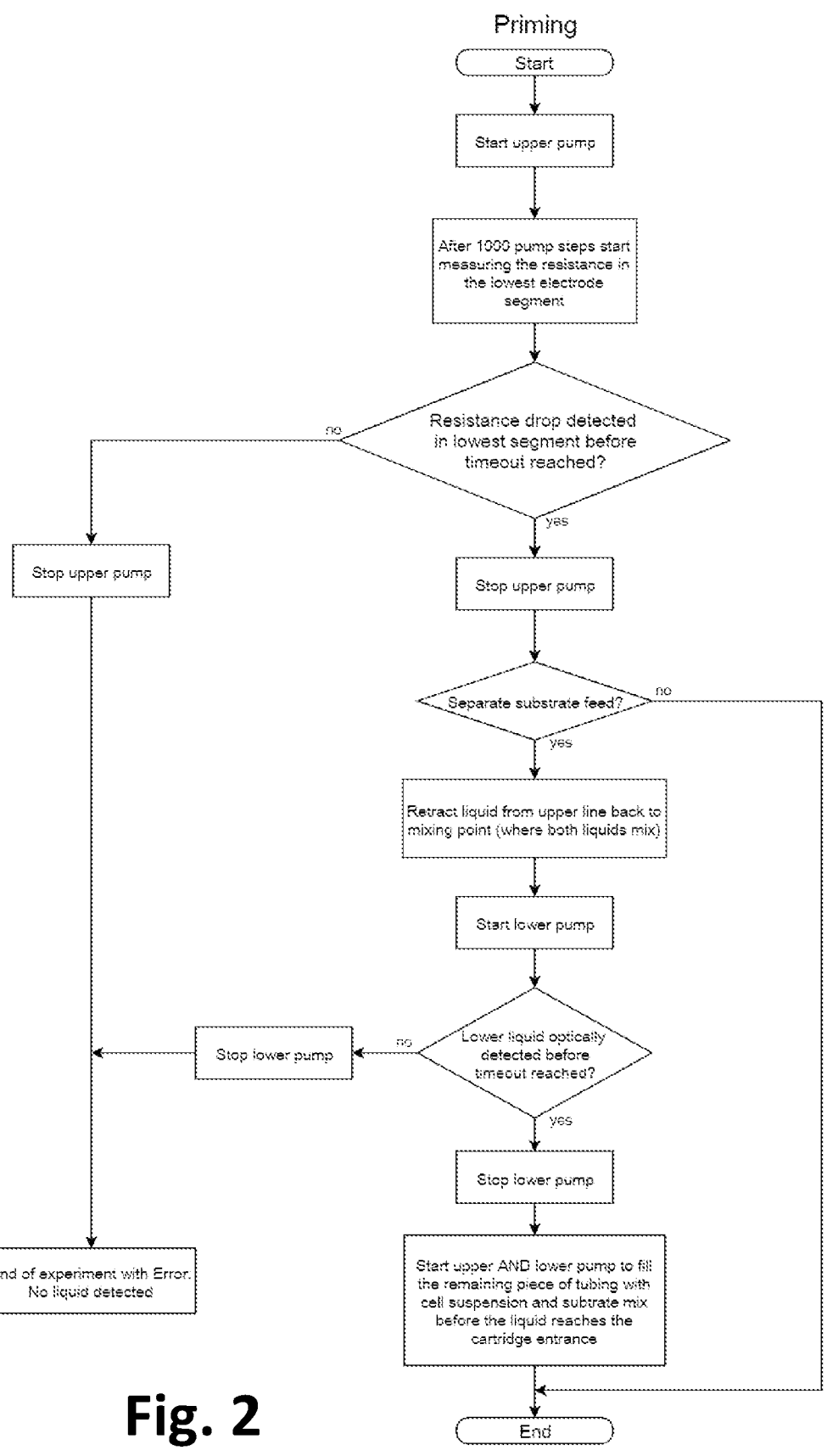
FIG. 2 shows a flow chart representing an exemplary sequence of the initial delivering procedure ("priming") of the method according to the invention.

FIG. 2 shows an exemplary sequence of the initial delivering procedure ("priming"). In order to be independent of the tubing length, the optical properties of the suspension and to avoid more complex measurements such as capacitive methods during the initial delivering procedure, the electrodes of the reaction chamber are used to observe liquid-based electrical changes inside the chamber to determine when the first fraction of the suspension has reached the reaction chamber. To this end, the initial delivering procedure ("priming") is started by starting a first pump (the "upper pump" as referred to in FIG. 2, the first pump being a peristaltic, stepper motor pump in this example) which pumps a suspension of cells, cell derivatives, organelles, sub-cellular particles and/or vesicles out of a first reservoir to a mixing point and then to an inlet port of the reaction chamber. The measurement of the electrical resistance at the first electrode of the chamber (the "lowest (electrode) segment" as referred to in FIG. 2) is started when a preset number of steps of the first pump has been performed. For example, pumping may start with 1,000 steps before starting the resistance measurement. This is to be immune to small liquid fractions moving and affecting the resistance at the very beginning (see FIG. 4, "initial drop of resistance"). If the resistance measured at the first electrode drops below a predetermined threshold within a preset timeout period (e.g. 60 seconds), the first ("upper") pump is stopped. For example, the resistance threshold value may be about 10 Ohms below the initially measured resistance value upon start of priming. As soon as the measured resistance at the first electrode drops by 10 Ohms, the suspension shall be considered as detected. That is, in this "priming" process the resistance near the inlet port between the first electrode and a grounding electrode is measured. If the infinite electrical resistance of the empty electroporation chamber falls below the predetermined threshold, it can be reliably indicated that the suspension has reached the electrode closest to the inlet port.

Figure 3:
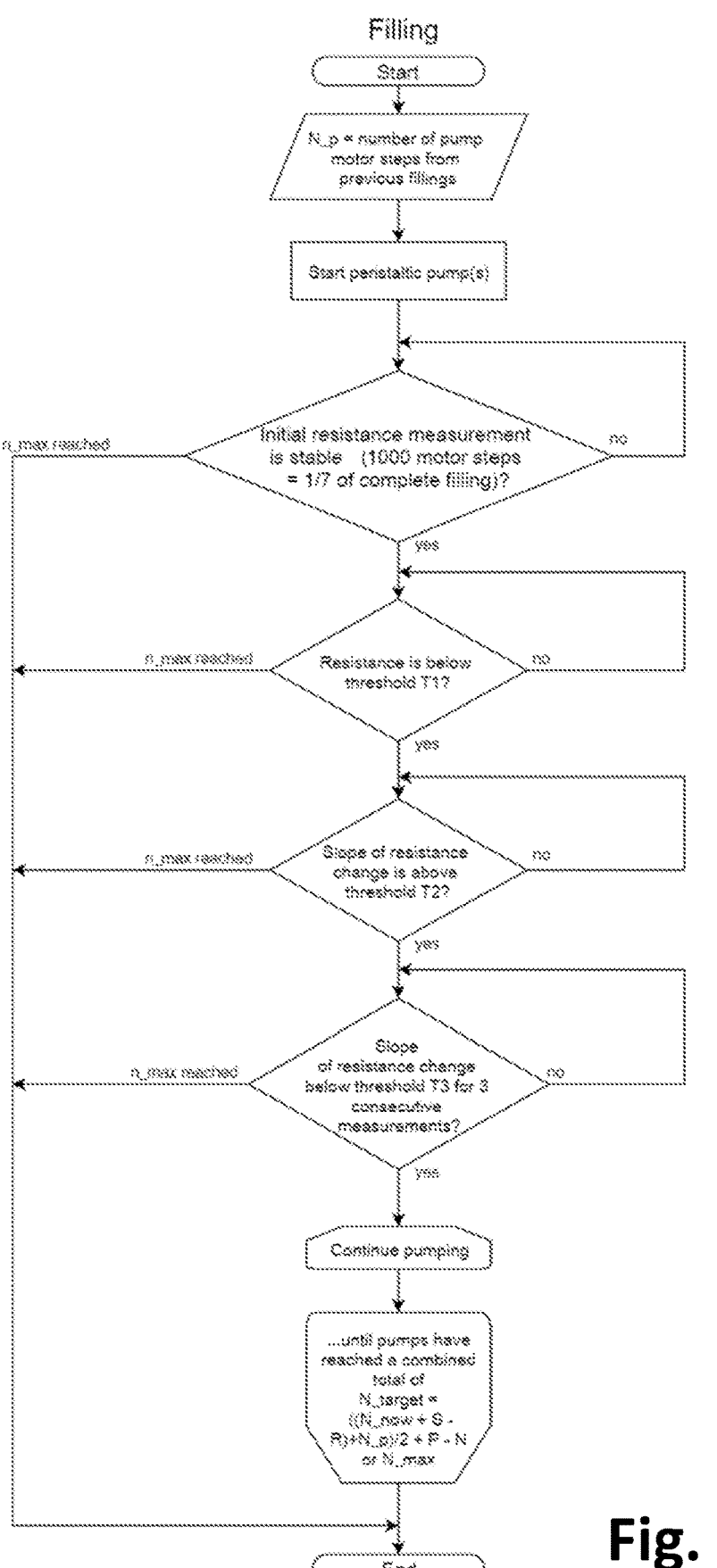
FIG. 3 shows a flow chart representing an exemplary embodiment of the method according to the invention including a filling procedure and a termination routine.

If the first pump is stopped due to a detection of a sufficient resistance drop and no separate substrate/probe feed is selected, the initial delivering procedure is terminated and the filling procedure is started (see FIG. 3). However, if no resistance drop is detected at the first electrode, the first ("upper") pump is stopped in this case as well and the routine is terminated with error indication. If the first pump is stopped due to a detection of a sufficient resistance drop and a separate substrate/probe feed is established, the suspension is retracted to the mixing point by reversing the running direction of the first pump. At the mixing point the suspension is mixed with the substrate or probe. To this end, a second pump is started (the "lower pump" as referred to in FIG. 2, the second pump being a peristaltic, stepper motor pump in this example) so as to pump the substrate or probe from a second reservoir to the mixing point. Mixing the suspension with the probe upstream of the inlet port and measuring the resistance upon entry of the mixture into the chamber ensures that the suspension is perfectly prepared for electroporation before it is introduced into the chamber. Incomplete mixture due to varying tubing length and different optical properties of the suspension can thus be avoided. Preferably, at least one optical sensor is disposed upstream of the mixing point at the tube connecting the second reservoir with the mixing point in order to detect the liquid comprising the substrate or probe. If no liquid is optically detected within a preset timeout period, the second "lower" pump is stopped and the routine is terminated with error indication. But if the liquid comprising the substrate/probe is detected, the second "lower" pump is stopped as well and the tubing connecting the mixing point with the inlet port is then filled with the mixture by both pumps running simultaneously until it reaches the inlet port (the "cartridge entrance"" as referred to in FIG. 2). The initial delivering procedure is then terminated and the filling procedure is started (see FIG. 3).

Figure 4:
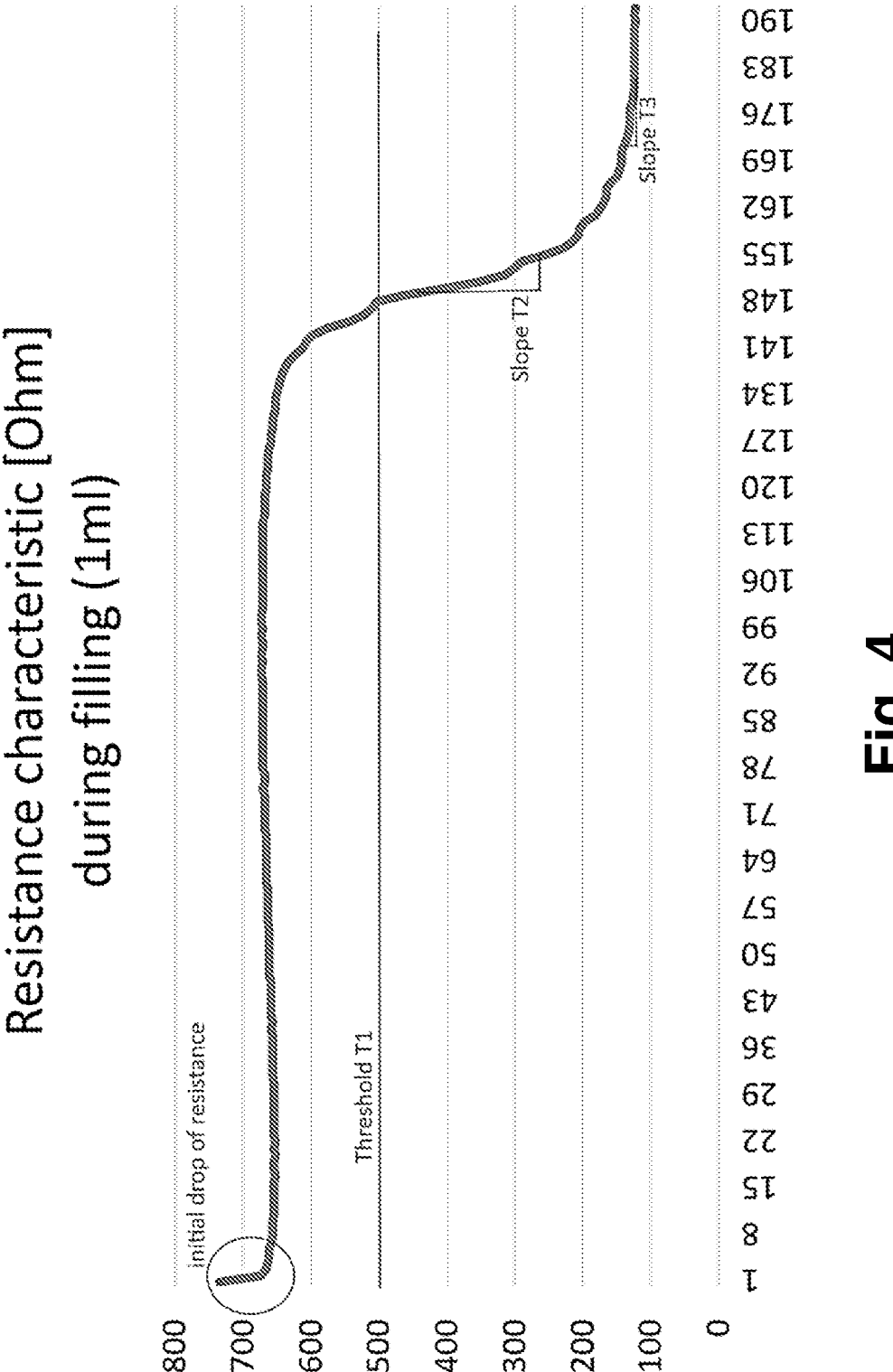
FIG. 4 shows a diagram representing an exemplary course of the electrical resistance during a filling procedure measured by an electrode at the outlet port of a device according to the invention.

FIG. 3 shows an exemplary embodiment of the filling procedure and termination routine according to the invention, while FIG. 4 shows a typical resistance characteristic during the filling procedure. According to the invention filling of the reaction chamber is controlled by monitoring the electrical resistant characteristic in the chamber at the outlet port (second electrode). Upon start of the filling procedure, at least one pump (e.g. first ("upper") and/or second ("lower") pump according to FIG. 2) pumps a certain volume of the suspension/mixture into the chamber. For example, if a peristaltic (stepper motor) pump is used, the pump is set to a predetermined number of motor steps (N_p). For the first filling (cycle) N_p is set to a default value and for all further fillings (cycles) N_p is set to a predetermined value based on values of previous fillings.

During the entire filling procedure the resistance value of the second electrode at the outlet port of the reaction chamber is measured continuously. Once the resistance falls below a predetermined value (limit "threshold T1"), the termination routine is initiated. If the system determines that a first slope of the change in resistance exceeds a first predetermined threshold (T2), the system waits for the slope to decrease again until a second slope of the change in resistance reaches a second predetermined threshold (T3) for at least two consecutive measurements. If these criteria are being met then the pump (which is at N_now steps) continues to rotate for another fix amount of steps (S). Since the effect of volume reduction is also affected by the energy of the voltage pulse delivered, this goes into the pump correction by reducing the target number of steps by R.

Extensive experiments have shown that variations in the correlation of resistance and filling level can be sufficiently reduced by setting the target pump steps for the current filling (if it is not the first filling cycle) to:

(Number of steps from previous filling "$N\_p$"+current standard detection target steps)/2+a fix value ($P$).

These experiments have still shown a deviation from the perfect filling amount that constantly increases from filling to filling. This is addressed by adding further steps N to the filling that are a product of a constant value and the current filling cycle:

$$N\_target = ((N\_now + S - R) + N\_p)/2 + P - N$$

After these additional pump steps have been performed, filling of the chamber is terminated. In addition, the number of steps for the pump cannot be higher than the steps from the previous filling (if it is not the first filling cycle). Accordingly, if a preset maximum number of pump steps (N_max) is reached, filling of the chamber is terminated.

T1 can be, e.g., set to 500 Ohm;

T2 can be, e.g., set to 50 Ohm/400 pump steps (system specific);

T3 can be, e.g., set to 20 Ohm;

S can be, e.g., set to 850;

R is set to a number of steps correlating with the voltage pulse energy;

P is an empirically determined value (e.g. 200);

N is set to the number of filling cycles, for example, multiplied by 20;

N_now is the current number of steps;

N_p is the previous combined number of steps (first pump+second pump);

N_target is the target number of steps (first pump+second pump combined) to complete the current filling.

FIG. 5 shows the outer side of an exemplary embodiment of a device 1 according to the invention and FIGS. 6 and 7 each show the inner side of one component of the device 1 according to FIG. 5. The device 1 comprises base members 2, 30, each base member 2, 30 representing a component of the device 1 which is assembled of two components (base members 2 and 30) that are attached to each other. At their outer side, the base members 2, 30 are each provided with connectors 31 for connecting conduits to the ports 7, 8, 10, 11 of a curved reaction chamber 6. One or more reservoirs for the suspension/probe to be processed and one or more containers for processed suspension can be connected to the connectors 31 via suitable conduits. The suspension can be charged into and discharged from the chamber 6 by means of a pumping element, e.g., a vacuum pump or a peristaltic pump or the like, which may be connected to the suspension circuit between the reservoir(s)/container(s) and the connectors 31. In order to render the device 1 compatible with common conduits and pumping systems, the connectors 31 can be Luer slip or Luer lock connectors.

The base member 30 further comprises a multitude of conductive areas 32 for providing electric connection to the electrodes 4, 5 in the chamber 6. The conductive areas 32 may comprise an electrically conductive polymer, in particular a polymer doped with electrically conductive material or an intrinsically conductive polymer. The conductive areas 32 are designed to provide an electrical connection between the electrodes 4, 5 and at least one electric contact point 33. In this embodiment the conductive areas 32 are holes in the base member 30 which are at least partially filled with the electrically conductive material. The conductive areas 32 are electrically coupled with at least one electric contact point 33 via at least one conductive path, e.g., copper tracks on a layer of the base member (not shown). The electric contact point 33 can be contacted by at least one electric contact, so as to provide direct or indirect electric connection to a power source and/or voltage pulse generator.

The base members 2, 30 each include a curved recess 3 which is provided with four electrodes 4, 5. According to a preferred embodiment of the device 1 the chamber 6 may comprise at least two segments, each segment comprising at least two electrodes, wherein the grounding (counter) electrode is a common electrode of at least two segments. That is, three of the electrodes are segment electrodes 4 while one electrode is a counter electrode 5. The base member 2 represents one component of the device 1 which is assembled of two components that are attached to each other, wherein at least the inner sides of these components are designed inversely. That is, the base member 2 and the base member 30 have mirror-inverted inner sides that are attached to each other so that the recesses 3 of base members 2, 30 form a chamber 6 for holding a suspension of cells, cell derivatives, organelles, sub-cellular particles and/or vesicles. In this chamber 6 an electric field can be applied to the cells, cell derivatives, organelles, sub-cellular particles and/or vesicles, e.g., for transferring biologically active molecules such as nucleic acids or proteins into the cells, cell derivatives, organelles, sub-cellular particles and/or vesicles. To this end, the electrodes 4, 5 of base member 2 and the corresponding electrodes 4, 5 of base member 30 establish electrode pairs, wherein the segment electrodes 4 of base member 2 and the oppositely arranged counter electrode 5 of base member 30 establish three electrode pairs while the counter electrode 5 of base member 2 and the three oppositely arranged segment electrodes 4 of base member 30 also establish three electrode pairs. In this configuration the counter electrode 5 of base member 2 and the counter electrode 5 of base member 30 are each common electrodes of three segments so that the chamber 6 comprises six segments, wherein each segment is provided with one segment electrode 4 and an area of one common counter electrode 5.

Two ports 7, 8 are disposed at one end 9 of the chamber 6 and two ports 10, 11 are disposed at the opposite end 12 of the chamber 6. At the "lower" end 12, one port of ports 10, 11 can be used as inlet port for charging the chamber 6 and the other port of ports 10, 11 can be either used as outlet port for discharging the chamber 6 or as additional outlet port for clearing the chamber 6. At the opposite end 9, one port of ports 7, 8 can be used as outlet port for discharging the chamber 6 and the other port of ports 7, 8 can be used as additional outlet port, either for discharging the chamber 6 or, e.g., for venting the chamber 6. Accordingly, in this exemplary embodiment, each end 9, 12 is provided with two ports 7, 8, 10, 11 through which the chamber 6 can be filled with the suspension and/or through which the suspension can be purged out of the chamber 6. Depending on the flow direction, one end of the chamber comprises at least one inlet port while the opposite end of the chamber comprises at least one outlet port. For example, if at least one of ports 10, 11 is used as inlet port and at least one of ports 7, 8 is used as outlet port, the electrode 4 next to the inlet port 10, 11 at end 12 is, by definition, a first electrode 20 (second sensor electrode) and the electrode 4 next to the outlet port 7, 8 at end 9 is, by definition, a second electrode 21 (first sensor electrode). Accordingly, in this exemplary embodiment, the electrical resistance for controlling the filling procedure is measured between the second electrode 21 of base member 30 and the grounding electrode 5 of base member 2. The measurement of the electrical resistance for controlling the initial delivering procedure is measured between the first electrode 20 of base member 2 and the grounding electrode 5 of base member 30. However, any other electrode configuration and/or chamber design can be realized as long as it is suitable to accomplish the method according to the invention as described above.

The invention claimed is:

1. A device comprising:

a chamber extending from a first end to an opposing end, at least a first electrode and a second electrode, at least one first grounding electrode and at least one second grounding electrode, at least one inlet port disposed at one the first end of the chamber; and at least one outlet port disposed at the opposing end of the chamber, wherein the first electrode and, oppositely arranged, the at least one first grounding electrode form a first electrode pair that is disposed within the chamber at the inlet port, and the second electrode and, oppositely arranged, the at least one second grounding electrode form a second electrode pair that is disposed within the chamber at the outlet port, and wherein at least the second electrode is a first sensor electrode that is operative to measure a first electrical resistance within the chamber between the second electrode disposed at the outlet port and the at least one second grounding electrode disposed at the outlet port.

2. The device according to claim 1, wherein the first electrode is a second sensor electrode that is operative to measure a second electrical resistance within the chamber between the first electrode disposed at the inlet port and the at least one first grounding electrode disposed at the inlet port.

3. The device according to claim 1, wherein the chamber comprises at least two segments, wherein each of the at least one first and the second grounding electrode is a common electrode of at least two segments and each segment is provided with one segment electrode and an area of one of the first and the second common grounding electrode.

4. The device according to claim 1, further comprising a control system, wherein the control system is operative to:

initiate a filling procedure wherein a suspension is charged into the chamber through the at least one inlet port, measure periodically, during the filling procedure, the first electrical resistance between the second electrode and the at least one second grounding electrode; initiate a termination routine based on a termination condition.

5. The device according to claim 4, wherein the termination condition comprises at least one of:

a change in the first electrical resistance between the second electrode and the at least one second grounding electrode, the first electrical resistance reaches a predetermined value, a first slope of the change in the first electrical resistance exceeds a first predetermined threshold, a second slope of the change in the first electrical resistance reaches a second predetermined threshold, wherein the second slope is lower than the first slope, a third slope of the change in the first electrical resistance, wherein the third slope is measured after the second slope is determined, and wherein the third slope is equal to or less than the second slope.

6. The device according to claim 4, further comprising:

a peristaltic pump operative to deliver the suspension into the chamber, wherein the control system is further operative to initiate a deferred termination in response to the termination condition, wherein the filling procedure continues for a time period based on a preset parameter associated with the peristaltic pump.

7. The device according to claim 6, wherein the preset parameter comprises a number of steps performed by the peristaltic pump, wherein the number of steps comprises a calculated number of steps (N_target) necessary to complete the filling procedure, wherein the calculated number of steps (N_target) is calculated according to an equation: $N\_target=(N\_p+N\_sts)/2+P$, wherein N_p represents a previous number of steps performed during a previous filling procedure, wherein N_sts represents a number associated with a current standard detection target, and wherein P represents an empirically determined number of steps.

8. The device according to claim 6, wherein the preset parameter comprises a number of steps performed by the peristaltic pump, wherein the number of steps comprises a second calculated number of steps (N_target) necessary to complete the filling procedure, wherein the second calculated number of steps (N_target) is calculated according to a second equation:

$$N\_target=((N\_now+S-R)+N\_p)/2+P-N,$$

wherein N_now represents a current number of steps, wherein S represents a preset number of steps, wherein R represents a preset number of steps correlated with an energy associated with an electrical voltage pulse, wherein N_p represents a previous number of steps performed during a previous filling procedure, wherein P represents an empirically determined number of steps, and wherein N represents a number of filling procedures multiplied by 20.

9. The device according to claim 4, wherein the control system is operative to initiate an initial delivering procedure, wherein the initial delivering procedure comprises:

mixing the suspension with a substrate or a probe to form a mixture, wherein the substrate or the probe is located at a mixing point upstream relative to the at least one inlet port; and detecting a resistance drop associated with the first electrode, charging at least one of the mixture or the suspension through the at least one inlet port into the chamber based on the resistance drop, wherein the electrical resistance is measured periodically within the chamber between the first electrode and the at least one first grounding electrode.

10. The device according to claim 9, wherein the resistance drop comprises a decrease of the electrical resistance in a range from about 5 Ohms to about 15 Ohms.

11. The device according to claim 10, wherein the resistance drop comprises a decrease of the electrical resistance of about 10 Ohms.

12. The device according to claim 9, wherein the initial delivering procedure initiated by the control system further comprises:

stopping the charging based on the resistance drop;

retracting a portion of the suspension toward the mixing point; and mixing the portion with the substrate or the probe before the control system initiates the filling procedure.

13. The device according to claim 9, wherein the control system is operative to: initiate the initial delivering procedure once before initiating the filling procedure.

14. The device according to claim 4, wherein the control system is operative to apply an electric field to the suspension within the chamber by:

supplying at least one voltage pulse through at least one of the first electrode or the second electrode after the filling procedure is terminated; and subsequently supplying a second voltage pulse to the suspension for a predefined number of cycles.

15. The device according to claim 1 further comprising a control system that is operative to measure the first electrical resistance between the second electrode and the at least one second grounding electrode.

16. A method comprising:

providing the device of claim 1 for controlling a filling level of a suspension within the chamber of the device;

starting a filling procedure wherein the suspension is charged into the chamber through the inlet port;

measuring an electrical resistance within the chamber between the second electrode and the at least one second grounding electrode during the filling procedure at several points in time;

and initiating a termination routine comprising terminating the filling procedure, wherein the termination routine is initiated depending on at least one change of the electrical resistance between the second electrode and the at least one second grounding electrode.

\* \* \* \* \*